United States Patent [19]

Horváth et al.

[11] Patent Number: 5,276,226
[45] Date of Patent: Jan. 4, 1994

[54] LOW TEMPERATURE HALOGENATION OF ALKANES

[75] Inventors: István T. Horváth, New Hope, Pa.; Raymond A. Cook, Bethlehem Township, Hunterdon County, N.J.; Gabor Kiss, Miami, Fla.

[73] Assignee: Exxon Research & Engineering Company, Florham Park, N.J.

[21] Appl. No.: 956,706

[22] Filed: Oct. 5, 1992

[51] Int. Cl.$^5$ .................. C07C 17/00; C07C 19/00
[52] U.S. Cl. .................... 570/253; 570/252
[58] Field of Search ................ 570/253, 252

[56] References Cited

U.S. PATENT DOCUMENTS

| | | | |
|---|---|---|---|
| 2,644,016 | 6/1953 | Furr et al. | 570/253 |
| 2,676,998 | 4/1954 | Kuntz et al. | 570/253 |
| 4,523,040 | 6/1985 | Olah | 570/253 |
| 4,746,760 | 5/1988 | Bergman et al. | 570/241 |
| 4,849,534 | 7/1989 | Bergman et al. | 556/23 |

OTHER PUBLICATIONS

Kushch et al., "Kinetics and Mechanism of Methane Oxidation in Aqueous Solution of Platinum Complexes," Nouveau J. de Chimie 7 (12) pp. 729–733 (1983).
Goldshleger et al., "Reactions of Alkanes in Solutions of Chloride Complexes of Platinum", Russian J. of Phys. Chem. 45 (5) pp. 785–786 (1972).
Shilov et al., "Activation of Saturated Hydrocarbons by Metal Complexes in Solution", Coordination Chem. Reviews 24 (2/3) pp. 97–143 (1977), Amsterdam.
Horvath et al., "Low Temperature Methane Chlorination with Aqueous Platinum Chlorides in the Presence of Chlorine" (Abstract #499), Am. Chem. Soc., Div. of Inorg. Chem., 204th ACS National Meeting, Washington, D.C., Aug. 23–28, 1992.

*Primary Examiner*—Werren B. Lone
*Attorney, Agent, or Firm*—Linda M. Scuorzo

[57] ABSTRACT

The invention relates to a process for selectively producing alkyl halides from alkanes, such as methane and ethane at relatively mild temperatures and pressures in an organic liquid phase in the presence of halogen and transition metal complex. The alkane may be neat if in a liquid form, or may be solubilized with a suitable organic solvent, if the alkane not a liquid at reaction conditions. The reaction is for a time, under conditions of temperature and pressure and in effective amounts that will permit the formation of alkyl halides. Optional hydrolysis to the corresponding alcohols may follow. The alkyl halides have utility as precursors for alternative fuels, such as methanol.

7 Claims, No Drawings

LOW TEMPERATURE HALOGENATION OF ALKANES

BACKGROUND OF THE INVENTION

1. Field of the Invention

The invention relates to a process for the halogenation of alkanes to alkyl halides in a homogeneous organic liquid phase, under mild conditions of temperature and pressure.

2. Description of Related Art

Halogenation of alkanes to alkyl halides, particularly chlorination to alkyl chlorides under relatively mild temperature and pressure offers the possibility for development of simple, low cost means for producing alkyl halides. Alkyl halides are known to those having ordinary skill in the art to have utility as a feedstock for more valuable commercial reactions. For example, methyl chloride and other alkyl halides have utility as an intermediate for production of alcohols, such as methanol, which itself is useful as an alternative, less environmentally damaging, fuel source. Additionally, methanol can be used as a feedstock for chemical reactions; for example, it can be used in reactions to yield gasoline or other hydrocarbons. More importantly, alcohol can be used as a transportation fuel source or as an additive to transportation fuels, particularly gasoline, to reduce hydrocarbon emissions and produce a more environmentally safe fuel.

The literature describes a number of processes for halogenating alkanes. However, unlike the processes described in the literature, applicants' process halogenates alkanes under mild temperature and pressure conditions in an organic liquid phase using a transition metal complex system.

SUMMARY OF THE INVENTION

The present invention relates to a process for halogenating alkanes to produce alkyl halides at relatively mild conditions of temperature and pressure in an organic liquid phase. The process comprises introducing into a reactor an effective amount of an alkane (either neat if the alkane may be maintained as a liquid under the conditions of the process of the present invention or in a suitable solvent), a halogen and a suitable transition metal complex (either added initially or formed in situ), which complex has a solubility in the organic liquid phase that is effective to halogenate the alkane, and reacting the same for a time and under conditions of temperature and pressure sufficient to form the corresponding alkyl halide(s). If an organic solvent is used, it should be one in which the alkane and the transition metal complex may be solubilized sufficiently to carry out the reaction, typically $CCl_4$ or perfluorohydrocarbons. Alkyl monohalides may be converted via hydrolysis to alcohols in a separate step using techniques known to one skilled in the art. Alkyl halides and their alcohol hydrolysis products have utilities as intermediates for alternative fuels production and as alternative fuels, respectively.

DESCRIPTION OF THE INVENTION

Alkyl halides, particularly alkyl chlorides such as methyl chloride, can be produced by a process which comprises contacting (i.e. introducing into a suitable reactor and reacting) an effective amount of an alkane, a halogen and a transition metal complex for a time, at a temperature and pressure and otherwise under conditions sufficient to produce the corresponding alkyl halide(s), and, optionally, hydrolyzing the resulting alkyl halide to the corresponding alcohol.

At low levels of conversion, the reaction acts selectively for monohalogenated products. The conditions of the reaction can be adjusted to obtain high conversion but selectivity for monohalogenated products may decrease.

The embodiments of the present invention may suitably comprise, consist or consist essentially of the elements disclosed, and the process may suitably be practiced in the absence of any step(s) not specifically disclosed as required.

The particular transition metal complex suitable for use herein may be prepared by methods known to ones ordinarily skilled in the art or obtained from commercial sources. All other starting materials may be obtained from commercial sources.

The alkanes suitably may be methane, ethane or higher alkanes, including cycloalkanes and mixtures thereof, so long as the alkane may be solubilized, dissolved or otherwise present in a form that is compatible with the liquid phase halogenation of the process of the present invention. Liquid alkanes may be introduced neat, if the alkanes remain liquid under the process conditions herein. When an alkane is present as liquid, an additional organic solvent is not required except if it is desired to adjust selectivity or control reaction rate. A suitable organic solvent is required if gaseous or another non-liquid alkane starting material is used, in order to provide the organic liquid phase for the reaction.

The halogen starting materials are introduced as a molecular halogen, preferably chlorine or bromine. It may be introduced into the system in gaseous or other form compatible with the process. If fluorine is used, care must be taken in handling to avoid explosive reactions.

The transition metal complex may be added to the system as a starting material or may be produced in situ from a compound consisting of a transition metal and a ligand capable of reacting to form the transition metal complex under the conditions disclosed herein. However, any complex so formed must be in whole or in part sufficiently soluble in the organic liquid phase to enable the reaction to occur, i.e., homogeneous with the system. Suitable ligands are carboxylates, halogenated carboxylates, alkoxides, and other ligands that are stable in a halogenating environment under the conditions of this invention. Suitable transition metal complex starting materials are those in which the transition metal is soluble in an organic liquid phase, e.g., platinum, palladium, cobalt, rhodium, iridium, ruthenium and nickel or mixtures thereof or, more preferably, platinum, rhodium, palladium. The complex may contain a halide, e.g., fluoride, chloride, bromide, or iodide or mixtures thereof, preferably a chloride. The preferable transition metal complex when used as a starting material is a complex having the formula $Pt(RCOCR'COR)_2$ where R and R' may be alkyl and aryl groups; wherein the alkyl or aryl may be partially or completely halogenated, or unhalogenated, preferably $Pt(CH_3COCHCOCH_3)_2$ and $Pt(CF_3COCHCOCF_3)_2$. When the R or R' is an alkyl it is preferably a methyl, ethyl, propyl and the like up to the limit of solubility of the material under the reaction conditions disclosed herein; and when R or R' is an aryl it is preferably phenyl, benzyl and the like up to the limit of solubility of the material under the reaction conditions disclosed herein. Because halogenation in the process of the present invention is carried out in the organic liquid phase the transition metal complex, if not initially soluble therein, should be one that may be rendered soluble therein by in situ halogenation in whole or in part to a degree that is sufficient to carry out the process of the present invention. Thus, the halogen starting material also may serve the function of solubilizing an initially insoluble or heterogeneous transition metal complex starting material or a transition metal and suitable ligand starting material to a degree that is effective to enable the liquid phase halogenation to occur.

The organic liquid phase may be provided by a suitable organic solvent in which the alkane may be solubilized, if the alkane is not in liquid form at the reaction temperature, or may be the neat alkane, if it is liquid under the conditions chosen. Suitably, organic solvents such as $CCl_4$ or perfluorohydrocarbons may be used. The solvent should be one in which the alkane can be halogenated without halogenating the solvent itself to any extent that interferes with the process itself. Such solvents may be chosen by one ordinarily skilled in the art.

Without wishing to be bound by any theory, it is believed that these reactions involve halogen radicals (as evidenced by selectivity of chlorination of n-hexane) and, therefore, suitable conditions particularly with relation to the use and handling of halogens and halides may be chosen by one skilled in the art given the teachings herein.

In all cases, the pressure and temperature of the reaction and concentrations of reactants should be such that the flash point of the gaseous reactants is not exceeded. Due regard should be given to the corrosive nature of the particular Group VIIA reactants used. Particularly in the case of fluorination of alkanes, reactions should be performed in high dilution, preferably in the presence of an inert gas, to minimize handling problems. For further conditions known to those ordinarily skilled in the art for carrying out reactions using halogens, see e.g., F. Cotton and G. Wilkinson, *Advanced Inorganic Chemistry. A Comprehensive Text*, 4th ed., Part 2, Ch. 17, p.p. 542-576 "The Group VII Elements, Fluorine, Chlorine, Bromine, Iodine and Astatine".

In the process of the present invention, halogenation of the alkanes is carried out under relatively mild conditions of temperature and pressure. The process of the present invention may suitably be carried out at any combination of temperature and pressure that is effective to maintain a liquid phase and to result in halogenation of the alkanes in that liquid phase as described herein. One skilled in the art may select the appropriate combinations to effect the process. Typically, halogenation may be carried out at a temperature range from about 20° C. to about 315° C., preferably from about 15° C. to about 200° C., more preferably from about 20° C. to about 150° C., depending on the particular reactants and conditions. The total pressure selected will vary based on the form in which the alkane and halogen are introduced into the system (e.g., liquid, gas). Generally, for gaseous halogens the pressure should be suitable to effect the process at the reaction temperature, which typically may be from about 1 atm to about 300 atm. Where, for example, the reaction is carried out using gaseous $Cl_2$ at about 20° C. to about 25° C., and a liquid hydrocarbon the preferable pressure range is from about 1 to about 6 atm.

Halogenation of alkanes to alkyl halides, according to the process of the present invention, may be carried out selectively, at low conversion. Ratios of starting materials generally affect reaction rate and may be chosen accordingly. Suitably, any effective ratio of halogen to hydrocarbon is acceptable. Typically, for liquid hydrocarbons a ratio of greater than or equal to about 1:1, preferably from about 1:1 to about 1:10, more preferably from about 1:1 to about 1:100. Generally, more halogen concentration increases reaction rate.

To avoid light-initiated radical reactions, the process should be carried out in the dark.

Specific reaction conditions and times for the present invention will depend on the particular combination of reagents used, the sample size, and the type of process (batch or continuous), but should be effective to permit the synthesis of alkyl halides. The selection of these particular reaction times, conditions and combination and concentrations of starting materials may be readily made by one ordinarily skilled in the art given parameters established by the the teachings herein. General background concerning, for example, the conditions necessary for the chlorination of methane can be found in J. S. Sconce, *Chlorine, Its Manufacture, Properties and Uses*, R. Landau and S. Fox, Chapter 12, "Chlorinated Methanes", pp. 334 to 375. Other halogenation reactions may be carried out similarly by one ordinarily skilled in the art.

The process of the present invention may be run in batch or may be operated continuously. The latter may be accomplished by removing on an ongoing basis the alkyl halides, recycling the complex containing the transition metal and regenerating the halogen by oxidation of the halogen containing by-products, HX (X=Cl, Br) of the reaction. The corresponding alcohol(s) of the alkyl halides may be produced by the hydrolysis of the resulting alkyl halides in a separate or subsequent hydrolysis step according to procedures known in the art.

The following examples are illustrative and not intended to limit the scope of the invention.

GENERAL

As used herein $Pt(hfac)_2$ means platinum (II) hexafluoroacetylacetonate; "hfac" means $CF_3C(O)CHC(O)CF_3$); and "$Pt(acac)_2$" means Pt(II) acetylacetonate.

EXAMPLE 1

Commercially available carbontetrachloride, chlorine, methane and $Pt(hfac)_2$ were used without further purification. The reaction was carried out at 125° C. in a 250 $cm^3$ polytetrafluoroethylene (PTFE) lined autoclave (Berghof, HR-200), the metal fittings were made of Hastelloy C-276. The thermocouple which was in contact in the reaction mixture was tantalum coated. Before the experiment, the autoclave was checked for and showed no activity.

100 mg $Pt(hfac)_2$ (0.16 mmole) in 20 ml of carbontetrachloride, 7.5 g of chlorine (105.8 mmole) and 5.1 g of methane (318.8 mmole) was used. The startup total pressure at 25° C. was about 35 bars. After loading the solution containing the $Pt(hfac)_2$ under nitrogen, the chlorine was charged and the unit was pressurized to the final pressure with methane. The reaction mixture was then warmed up to 125° C. and kept at that temperature for 2 hours. After cooling the unit back to 25° C., an evacuated high pressure bomb was connected to the autoclave and the gas content was condensed into the bomb using liquid nitrogen. After warming the filled bomb to 25° C., the content of the bomb was weighed and its pressure was read. The composition of the gas and the liquid phase was determined by gas chromatography. The mass balance that was based on the gas load and the sampling data showed that 95% of the gas load was recovered and identified in the gas sample. The GC analysis of the product gave 3.3% conversion of the methane. The chlorinated products were identified as methyl chloride (94%) and dichloromethane (6%). The GC analysis of the liquid phase detected only trace levels of chloroform.

EXAMPLE 2

Commercially available chlorine, cyclohexane, carbontetrachloride and Pt(hfac)$_2$ were used without further purification. The liquids were deaerated. All procedures were carried out under nitrogen, using glove box/Schlenk technique. The reaction was performed at 25° C. in a 9 ml Pyrex glass high pressure tube which was fully covered with black tape. Before the experiment, the tube was checked for and showed no activity by loading all but Pt(hfac)$_2$.

3.0 ml CCl$_4$, 0.5 ml (4.6×10$^{-3}$ moles) cyclohexane, 0.4 g (5.6×10$^{-3}$ moles) and 11 mg (18.1×10$^{-6}$ moles) Pt(hfac)$_2$ was used. After 3 hours, the content of the tube was treated in the dark with aqueous Na$_2$SO$_3$/Na$_2$CO$_3$ solution in order to remove chlorine excess before analysis. The GC analysis of the product showed 9.5% conversion of cyclohexane to chlorinated products (approximately 25 turnovers) with 90% selectivity for monochlorocyclohexane. Besides the monochlorinated product, a mixture of dichlorocyclohexane isomers were identified.

EXAMPLE 3

Reaction under the same conditions as in Example 2, but with 3.0 ml neat cyclohexane gave similar results with 95% selectivity and about 30 turnovers.

EXAMPLE 4

Commercially available chlorine, n-hexane and Pt(hfac)$_2$ was used without further purification. N-hexane was deaerated before use. The procedures were carried out under nitrogen, using standard glove box/Schlenk technique. The reaction was performed at 25° C. in a 9 ml Pyrex glass high pressure tube which was fully covered with black tape. The tube was checked for and showed no activity before the experiment.

3 ml n-hexane, 0.4 g chlorine (approximately 4 bars) and 11 mg Pt(hfac)$_2$ was used. After 4.5 hours, the content of the tube was treated in the dark with aqueous Na$_2$SO$_3$/Na$_2$CO$_3$ solution in order to remove chlorine excess before analysis. The GC analysis of the product showed 4% conversion of the n-hexane to chlorinated products. The monochlorinated product represented 33% of the total product. 1-chlor-n-hexane represented 23% of the total monochlorinated product.

EXAMPLE 5

Procedure and starting materials were the same as in Example 4, except that Pt(acac)$_2$ was used instead of Pt(hfac)$_2$. [Pt(acac)$_2$ is insoluble in n-hexane. However, in the presence of Cl$_2$ the acac ligand is chlorinated and the complex formed as a result are sufficiently soluble in the organic phase so the Pt(acac)$_2$ starting material was loaded in powder form into a Pyrex high pressure glass tube.

3 ml n-hexane, 0.4 g chlorine (approximately 4 bars) and 4 mg Pt(acac)$_2$ (10×10$^{-6}$ moles) was used. After 4.5 hours, the contents of the reaction vessel was treated as in Example 4. At the end of the experiment, after the removal of the excess chlorine, an orange yellow organic phase was obtained which clearly indicated that the starting Pt(acac)$_2$ was chemically altered and in situ formed a complex that dissolved in the organic phase to form a homogeneous system. $^1$H and $^{13}$C NMR spectra of the formed Pt complex clearly indicated the formation of a wide range of chlorinated acetylacetonate ligands coordinated to Pt(II). The GC analysis of the orange yellow product solution showed 25% conversion of the n-hexane load to chlorinated products. The monochlorinated product represented 89% of the total product. 1-chlor-n-hexane represented 23% of the total monochlorinated products.

EXAMPLE 6

Procedure and starting materials were the same as in Example 5, except that 40 mg (1×10$^{-6}$ moles) Pt(acac)$_2$ was treated before the experiment with chlorine in 3 ml dichloromethane. After the removal of dichloromethane, a dark orange solid formed.

0.4 g chlorine and 3.0 ml saturated n-hexane solution of chlorinated Pt(acac)$_2$ was used. After 1.8 hours, the product was treated as in Example 5. The GC analysis showed 5% conversion of n-hexane to chlorinated products. The monochlorinated product represented 85% of the total conversion and the terminally chlorinated product represented 24% of the total monochlorinated products.

What is claimed is:

1. A process for halogenating alkanes to form alkyl halides, which comprises:
   an effective amount of an alkane or mixtures thereof, a halogen or mixtures thereof, and a transition metal complex having the formula Pt(RCOCR'OR)$_2$ wherein R and R' are each selected from the group consisting of alkyls, aryls, halogenated alkyls and halogenated aryls for a time, and at a pressure and temperature that is effective to maintain an organic liquid phase; and
   reacting the alkane, halogen and transition metal complex in the organic liquid phase to produce an alkyl halide corresponding to the alkane and having solubility in the organic liquid phase.

2. The process of claim 1 wherein the transition metal complex is selected from the group consisting of Pt(CH$_3$COCHOCH$_3$)$_2$ and Pt(CF$_3$COCHCOCF$_3$)$_2$.

3. The process of claim 1 wherein the temperature is in a range from about 15° C. to about 315° C.

4. The process of claim 1 wherein the alkane is methane or ethane.

5. The process of claim 1 wherein the alkane is a liquid.

6. The process of claim 1 wherein the alkane is a solid or a gas and is solubilized in a suitable organic solvent that is inert to the halogen.

7. The process of claim 1 wherein the transition metal complex is selected from the group consisting of Pt(CH$_3$COCHCOCH$_3$)$_2$ and Pt(CF$_3$COCHCOCF$_3$)$_2$, the alkyl halide is alkyl chloride and the added halogen is Cl$_2$.

* * * * *